United States Patent
Beretta et al.

(10) Patent No.: US 6,368,298 B1
(45) Date of Patent: Apr. 9, 2002

(54) PREPARING AUTOLOGOUS FIBRIN GLUE

(75) Inventors: Roberto Beretta, Via Rho 8, Milan; Sergio Lodi, Merate, both of (IT)

(73) Assignee: Roberto Beretta, Milan (IT)

( * ) Notice: Subject to any disclaimer, the term of this patent is extended or adjusted under 35 U.S.C. 154(b) by 0 days.

(21) Appl. No.: 09/446,729

(22) PCT Filed: Jun. 24, 1998

(86) PCT No.: PCT/IT98/00173
§ 371 Date: Mar. 3, 2000
§ 102(e) Date: Mar. 3, 2000

(87) PCT Pub. No.: WO98/58689
PCT Pub. Date: Dec. 30, 1998

(30) Foreign Application Priority Data

Jun. 24, 1997 (IT) .......................... MI97A1490

(51) Int. Cl.[7] .......................... A61M 37/00; A61M 5/00; A61K 35/12; A61K 35/16
(52) U.S. Cl. .......................... 604/4.01; 604/6.01; 604/7; 604/522; 210/782; 424/520; 424/530
(58) Field of Search .......................... 604/4.01, 5.01, 604/6.01, 6.04, 6.07, 57, 81–85, 89, 7, 264–65, 522; 422/44, 61; 210/645, 781–82, 787, 789; 424/443–44, 484, 488, 520, 529–30; 530/380–82; 606/213–15

(56) References Cited

U.S. PATENT DOCUMENTS 5,030,215 A * 7/1991 Morse et al. ................ 604/410
5,585,007 A * 12/1996 Antanavich ................ 210/782
5,733,545 A * 3/1998 Hood ........................ 424/93.72
6,063,297 A * 5/2000 Antanavich ................ 210/782

FOREIGN PATENT DOCUMENTS

| EP | 0592242 A1 | * | 4/1994 | ........... A61L/25/00 |
| WO | WO 94/22503 | * | 10/1994 | ........... A61L/25/00 |
| WO | WO 95/12371 | * | 5/1995 | ........... A61F/13/00 |
| WO | WO 96/17871 | * | 6/1996 | ........... C07K/14/75 |
| WO | WO 96/27397 | * | 9/1996 | ........... A61L/25/00 |

OTHER PUBLICATIONS

Wolf, Der konzentrierte autologe Gewebekleber, Spring 1983, Arch Otorhinolaryngol, 237: pp. 279–283.*

Arch Otorhinolaryngol, vol. 237, 1983, G. Wolf, "Der konzentrierte autologe Gewebekleber", p. 276–p. 283; p. 280; paragraphs 3–6; p. 281, paragraphs 1–3.

* cited by examiner

Primary Examiner—Angela D. Sykes
Assistant Examiner—Patricia Bianco
(74) Attorney, Agent, or Firm—Michael Best & Friedrich

(57) ABSTRACT

A method of preparing a solid-fibrin web is disclosed. The method includes drawing blood from a patient, separating plasma from the blood, contacting the plasma with a calcium-coagulation activator and concurrently coagulating and centrifuging the plasma to form the solid-fibrin web. The solid-fibrin web is suitable for regenerating body tissue in a living organism.

22 Claims, No Drawings

PREPARING AUTOLOGOUS FIBRIN GLUE

The present invention relates to a kit and a method for preparing autologous fibrin glue, and particularly to a sealed container ready to use being provided with a coagulation activator suitable for obtaining autologous fibrin glue.

The fibrin glue is known to be a haemoderivative largely used as a topical surgical adhesive or an haemostatic agent. Several kits are available on the market containing concentrated fibrinogen from donors, associated to a proteic activator of human or animal origin, such as thrombin or batroxobin, for obtaining eterologous fibrin glue.

Such known kits involve the use of material of human or animal origin, which. owing to its origin, could result in possible viral contamination and in serious risks for the receiver of the fibrin glue. In the past the authorities have been several times compelled to suspend from the trade or even to ban the haemoderivatives obtained by using material of human or animal origin. Furthermore, rejection cases are known from the literature resulting from the reimplant in the patients of fibrin produced by using human or animal proteins. Such cases are indeed due to the eterologous origin, with respect to the receiver organism, of the sealant protein being reimplanted or some of the components used for preparing it.

The autologous fibrin glue, i.e. obtained from the blood of the patient himself, is more reliable with respect to the rejection and/or infection risks. Several procedures have already been described for obtaining extemporary autologous fibrin glue, but no "ready to use" kit is by now available on the market although some relevant references can be found in the patent literature.

For example U.S. Pat. No. 5,733,545 discloses a plasma-buffy coat concentrate to be combined with a fibrinogen activator to form a platelet glue wound sealant. The method disclosed in this patent allows to process blood of the patient for obtaining autologous fibrin glue, but it comprises the use of thrombin or batroxobin as fibrinogen activator. These activators are of human or animal nature and therefore still involve the risk o reject and/or viral infections for the patient.

U.S. Pat. No. 5,585,007 discloses a method and an apparatus for making concentrated plasma to be used as a tissue sealant. The method consists in separating plasma from whole blood and removing, water from said plasma by contacting it with a concentrator to provide concentrated plasma which can be thereafter coagulated with a solution containing, thrombin and calcium. The apparatus comprises a first centrifuge separator in a first chamber, a concentrator included in a second chamber communicating with the first chamber, and a second separator. The method disclosed in this prior art reference requires a long time for obtaining the plasma concentrate necessary for the subsequent preparation of autologous fibrin glue and the apparatus is expensive and not disposable.

The object of the present invention is therefore to provide a ready to use kit, allowing to rapidly obtain autologous fibrin glue and particularly not resulting in viral infections and/or rejection cases when used in surgery.

Such an object is achieved by using a coagulation activator, being neither of human nor of animal origin, but being an inorganic compound which therefore cannot be infected and does not result in rejection.

The "ready to use" kit according to the present invention comprises a sealed container containing calcium chloride as coagulation activator, Calcium chloride activates the fibrin present in patient's plasma when this is introduced into the sealed container.

The kit according to the present invention has the great advantage of allowing the preparation of autologous fibrin glue which may be used with no risk of viral infections or rejection cases. Another advantage of the kit according to the present invention is that it allows the preparation of autologous fibrin glue from patient's plasma in a very short time and in the desired form of clots or membrane or spray. Still another advantage of the kit ready to use according to the present invention is to allow the autologous fibrin glue to be obtained at costs proportionally lower with respect to the known systems.

Further advantages of the kit according to the present invention will be evident to those skilled in the art from the following detailed description of some embodiments thereof.

As container suitable for the kit according to the present invention can be used for example a glass container for antibiotics as hereinafter described in Example 1. Also glass or plastic test-tubes may be used. The preferred volume of the container is from 5 to 15 ml. The test-tubes have preferably a diameter ranging from 12 to 16 mm and a height ranging from 75 to 100 mill. The container should be suitably thick in order to withstand the stresses resulting from the pressure difference between its inner space and the atmosphere when it is evacuated. Hemispherical or conical bottom tubes are preferably 0.7 mm thick, flat bottom tubes 1 mm thick. The plastic containers are preferably made of transparent acrylic resin, 0.2–0.8 mm thick, in order to ensure the vacuum keeping for at least 12 months after production. The plastic test-tubes, after the preparation, are preferably introduced into a tin-foil vacuum air-tight container having a heat-sealed inner polyethylene layer, in order to ensure a perfect air-tightness until the date of use.

It should be noted that the evacuation of containers or test-tubes is advisable, however not necessary for putting the present invention into practice.

The containers or test-tubes are sealed by rubber or silicon pierceable caps, being suitable to ensure the container to be perfectly air-tight and to allow the vacuum plugging after the introduction of the chemical components and before the steam sterilization step.

After the sealing, the containers may be sterilized under steam at 121° C. for 30 minutes. The sterilization may be carried out also by irradiation with gamma rays.

As a fibrin stabilizer tranexamic acid can be used, but also pure and crystalline epsilon-amino-caproic acid is suitable to this purpose. The amount will be about 1 g when using a 25 ml container, suitable for a plasma amount of 20 ml. Sometimes it is not necessary to use a fibrin stabilizer.

As a coagulation activator solid $CaCl_2.2H_2O$ is used in the kit according to the present invention. For example, 11.76 mg, of $CaCl_2.2H_2O$ will be introduced in a 5 ml container, by using a precision dosimneter (maximum error: 1–2 mg), in order to prevent polluting foreign components to be introduced.

In case of a 15 ml container for a plasma amount of 12 ml, the solid dehydrated calcium chloride amount to be introduced will be as high as 35.28 mg, while the tranexamic acid amount will proportionally be as high as 300 mg of crystals.

In case of a 25 ml container for a plasma amount of 20 ml, the dehydrated calcium chloride amount to be introduced will be as high as 58.9 mg, while the tranexamic acid amount will proportionally be as high as 500 mg of crystals.

Besides the dehydrated form used in the Examples, the calcium chloride may be in any other suitable form available on the market, e.g. as $CaCl_2.6H_2O$. Also a solution of this salt can be used, as described in Example 1.

EXAMPLE 1

In a 5 ml glass container for antibiotics, being sealable under vacuum, made of transparent white glass, inert and I mm thick were introduced 100 mg of tranexamic acid, acting as fibrin stabilizer. The synthetic tranexamic acid, being more than 98% pure, is put on the market by the American company Sigma Inc. Separately, a 1 M $CaCl_2$ solution was prepared, by weighing on a precision balance 147.0 g of $CaCl_2.2H_2O$ (>99% pure), from the same American company Sigma Inc, This salt was dissolved in exactly 1 liter of ultrapure apirogenic distilled water, for a few minutes at room temperature, under frequent stirring. By using a precision piston dispenser, having a dispensing precision ol ±5% (Eppendotf like), 80 μl of the activator solution were introduced in the glass container. In this step, at the same time as the dispensing, a filtering was carried out by using a 0.22 μm Millipore sterilizing filter, while carefully preventing possible contamination from powders or filaments of any kind. Finally the glass container was plugged with a rubber cap being pierceable and plugable under vacuum, while minding not to completely plug tile container, so as to allow the subsequent vacuum plugging and possibly a further sterilization by using gas. The container was then introduced into a suitable device for vacuum plugging, while preventing any possible contamination from solid particles in the atmosphere (ULPA or HEPA filtration in sterile chamber). A vacuum as high as 4 ml was applied, by using a membrane vacuum pump and a micrometric control, to the inner atmosphere of the device. In order to control the vacuum level in the inner atmosphere, a precision vacuometer was used (precision ±1 mbar). Finally, without discharging, the device, the container was plugged under vacuum, to be thereafter recovered for the use as described in the following Example.

EXAMPLE 2

10 ml of venous blood were drawn from a patient according to the provisions of the qualitative standards for clinical analysis, e.g. by using VACUTAINER™ sterile test-tubes, added with a 0.106 M sodium citrate solution. For this purpose also test-tubes added with disodium or dipotassium ethylenediaminetetraacetate (EDTA) can be used. The sample was carefully kept sterile during the blood drawing. Finally, the sample was gently shaken for wholly mixing the components, thereby ensuring the anticoagulating action of sodium citrate. The test-tube was then introduced in a suitable centrifuge, while carefully balancing the rotor weight in order to prevent the same centrifuge to be damaged. Once the lid is sealed, the sample was centrifuged at 3500 rpm tor 15 minutes, thereby separating the red cells (being thicker) from the citrated plasma (supernatant). In this case the plasma yield, mainly depending upon the characteristics of the donor blood, was as high as 55%. The test-tube containing, the separated plasma was kept plugged in sterile conditions and was placed vertically in a stand for recovering the plasma itself. In this step care was taken not to shake the test-tube, in order to prevent the mixing of the two phases separated in the centrifugation. The outer portion of the test-tube cap was then sterilized by using denatured alcohol and then a sterile needle, being connected to a sterile syringe, was introduced in the test-tube cap. The needle was brought up to 3–4 mm apart from the separating meniscus of the two phases, and 4 ml of plasma were drawn. By using the same needle, the cap of the container according to the present invention, which had been prepared as described in Example 1, was pierced, having been previously sterilized by using alcohol. As soon as the needle pierced the cap, the citrated plasma contained in tile syringe was completely sucked into the container. This was gently shaken and, after about 2 minutes at 37° C., a clot of sterile autologous fibrin glue was obtained, ready to be immediately used,

EXAMPLE 3

About 18 ml of venous blood were drawn from a normotype 49 years-old patient by using 5 ml sodium citrate VACUTAINER™ test-tubes, taking care to shake gently just after the drawing of the sample. The so taken blood was immediately subjected to centrifugation (15 min. at 2500 rpm) to separate the plasma. The plasma (12 ml) was carefully transferred into two 10 ml test-tubes, containing 120 μL of $CaCl_2$ (10 g/100 ml) each, which had been prepared as described in Example 1, but without using tranexamic acid. After mixing the plasma with the activator, the test-tubes were centrifuged for 30 min. at 3000 rpm, finally obtaining two massive fibrin samples which were inserted, with all sterility precautions, within 2–3 hours from preparation, in the large vesicular mandibular cavity resulting from extraction of impacted left canine and right second incisor, as well as from abscission of the cyst present in the central area of the incisor teeth. Finally the gingival edges were closed with eight stitches. A radiographic check 15 days after showed the fibrin still in its position, apparently intact. Histology 7 months after proved the complete replacement of the fibrin with bony tissue, with a better post-operative course than with traditional methods, requiring over 12 months to achieve the same result. Since no antifibrinolytic agent had been used for the preparation of autologous fibrin, it can be stated in this case that said additive was useless for the specific purpose.

EXAMPLE 4

To produce an adhesive fibrin glue 12 ml of plasma, obtained as in Example 3, were transferred, with all the measures in order to preserve sterility, into a 20 ml container according to the present invention, prepared as described in Example 1.

After careful stirring, the mixed plasma was poured on a sterile glass slide, of the kind used in chemical laboratories, where the plasma was mixed with sterile and very pure calcium carbonate of coralline origin (BIOCORAL™-INOTEBS S.A. France), or with calcium fluoride (>98% Sigma Inc.). These calcium salts are both well known to the skilled in the art as stimulators of fibroblasts.

By mixing one part of the plasma with one part of calcium carbonate, (eg.: 2 ml with 500 mg) a malleable, sterile and adhesive paste was obtained and used as a filler for subgingival spaces or different cavities after abscission of infected mucous sacs. The paste, positioned so as to fill the empty spaces, formed in a few minutes a it solid fibrin web acting as a haemostatic plug and created an autologous biological substrate supporting the mucous edges in position and where later migration of connectival cells started.

EXAMPLE 5

To obtain a membrane of fibrin glue 20 ml of plasma, obtained as in Example 3, were put in a 25 ml, flat-bottomed container according to tile present invention prepared as in Example 1. After the usual careful stirring, the container was centrifuged for 40 min. at 4000 rpm with a swing-out rotor. At the end of the centrifuging operation, from the bottom of the test tube a white-colored, very compact and tensile-strong membrane was recovered, having the same size as the bottom of the test-tube (24 mm diam.) and thickness of 3 mm. This autologous membrane, owing to its compactness and strength, was used as a holding and separating membrane in dental and general surgery, as a substitute for porous synthetic membranes. The obtained membrane can be sterile stored for several days at 4° C.

EXAMPLE 6

To obtain large-sized membranes of fibrin glue about 200 ml of citrated plasma were drawn from a patient, collected and separated in a double transfusion bag. The plasma was subjected to cryoprecipitation by freezin at −80° C. for 12 hours, defreezing being carried out overnight at 4° C. (this procedure is well known to those skilled in the art). The same morning the plasma obtained by this procedure was subjected to centrifugation for 15 min. at 5000 rpm at 4° C. to obtain about 20 ml of cryoprecipitate. After careful removal of the supernatant by using a pressing device (e.g. XP100 of the company Jouan S.A. France) the cryoprecipitate was taken up with 20 ml of whole plasma of the same patient. The resulting 40 ml were put in a 35 mm diameter, flat-bottomed sterile polypropylene container according to the present invention, containing the suitable quantity of activator, as described in Example 1. After careful shaking, the container was centrifuged for 40 min. at 5000 rpm to obtain a membrane as in Example 5, but more compact and tensile-strong owing to the higher content of fibrin. Said membrane too can be stored in sterile form for several days at 4° C.

The membrane obtained by the method described in Example 5, in addition to utilization described in Example 4, can be used as a substrate for the culture in vitro of dermal cells of the same patient, in order to obtain grafts to be transplanted in case of very serious scalds.

Membranes of a good quality useful for the above mentioned purposes can be obtained also from whole separated plasma directly transferred into the container according to the present invention. The obtained membrane will be thinner than the above described one, but still useful for surgical uses and as a substrate for cellular growth.

EXAMPLE 7

To obtain spray fibrin starting from a cryoprecipitate as in Example 5, 20 ml of cryoprecipitate were taken up with 10 ml of whole plasma at room temperature and gently shaken, to complete dissolution. The resulting plasma was carefully transferred into a 50 ml container according to the present invention prepared as in Example 1, shaking gently for a perfect mnixing of the components. After 120 sec. at room temperature, the test-tube was connected to a Venturi-type sterile air compressor, known to those skilled in the art, to be uniformly distributed on the surface of a bleeding organ being subjected to surgery (lung, heart, spleen, arterious anastomosis). The concentrated plasma, containing concentrated fibrinogen, thrombin, calcium ions and other coagulation enzymes, distributed over the organ, coagulated within a few seconds, owing also to tissue coagulation activating enzymes present in the endothelium of the patient creating a fibrin film having a protective haemostatic function. The surgical operation was therefore concluded with the reduction of internal haemorrhages and so avoiding further blood transfusions or complications.

What is claimed is:

1. A method of preparing a solid-fibrin web, the method comprising:

drawing blood from a patient;

separating plasma from the blood;

contacting the plasma with a calcium-coagulation activator; and concurrently coagulating and centrifuging the plasma to form the solid-fibrin web, the solid-fibrin web being suitable for regenerating body tissue in a living organism.

2. The method of claim 1, whereby concurrently coagulating and centrifuging the plasma to form the solid-fibrin web alleviates the need to first pre-concentrate the plasma by removing water therefrom before contacting the plasma with the calcium-coagulation activator.

3. The method of claim 2, wherein the calcium-coagulation activator is selected from calcium chloride, calcium fluoride, calcium carbonate and combinations thereof.

4. The method of claim 1, whereby concurrently coagulating and centrifuging the plasma to form the solid-fibrin web alleviates the need to compress the solid-fibrin web and extract serum therefrom after the solid-fibrin web has been formed.

5. The method of claim 1, further comprising contacting the blood with an anticoagulant before separating plasma from the blood.

6. The method of claim 5, wherein the anticoagulant is a calcium-binding agent.

7. The method of claim 1, wherein the anticoagulant is selected from sodium citrate, ethylenelendiaminetetraacetic acid disodium salt, ethylenelendiaminetetraacetic acid dipotassium salt and combinations thereof.

8. The method of claim 1, wherein the solid-fibrin web is autologous.

9. A method of preparing a solid-fibrin web, the method comprising:

drawing blood from a patient;

separating plasma from the blood;

contacting the plasma with a calcium-coagulation activator; and coagulating and centrifuging the plasma to form the solid-fibrin web in a manner which alleviates the need to first pre-concentrate the plasma by removing water therefrom before the plasma is contacted with the calcium-coagulation activator, the solid-fibrin web being suitable for regenerating tissue in a living organism.

10. The method of claim 9 whereby contacting the plasma with a calcium-coagulation activator takes place in the presence of platelets and whereby the manner in which the plasma is coagulated and centrifuged to form the solid-fibrin web alleviates the need to subsequently compress the solid-fibrin web and extract serum therefrom after the solid-fibrin web has been formed.

11. The method of claim 9, whereby coagulating and centrifuging the plasma to formn the solid-fibrin web are performed concurrently.

12. The method of claim 9, wherein the calcium-coagulation activator is selected from calcium chloride, calcium fluoride, calcium carbonate and combinations thereof.

13. The method of claim 9, further comprising contacting the blood with an anticoagulant before separating plasma from the blood.

14. The method of claim 13, wherein the anticoagulant is a calcium-binding agent.

15. The method of claim 13, wherein the anticoagulant is selected from sodium citrate, ethylenelendiaminetetraacetic acid disodium salt, ethylenelendiaminetetraacetic acid dipotassium salt and combinations thereof.

16. The method of claim 9, wherein the solid-fibrin web is autologous.

17. A method of regenerating tissue in a living organism, the method comprising:
- drawing blood from the organism;
- separating plasma from the blood;
- contacting the plasma with a coagulation activator;
- concurrently coagulating and centrifuging the plasma to form a solid-fibrin web; and
- contacting an affected area of the living organism with the solid-fibrin web in order to regenerate tissue in the affected area.

18. The method of claim 17, whereby concurrently coagulating and centrifuging the plasma to form the solid-fibrin web alleviates the need to first pre-concentrate the plasma by removing water therefrom before contacting the plasma with the calcium-coagulation activator.

19. The method of claim 17, whereby concurrently coagulating and centrifuging the plasma to form the solid-fibrin web alleviates the need to compress the solid-fibrin web and extract serum therefrom after the solid-fibrin web has been formed.

20. The method of claim 17, wherein the calcium-coagulation activator is selected from calcium chloride, calcium fluoride, calcium carbonate and combinations thereof.

21. The method of claim 17, further comprising contacting the blood with an anticoagulant before separating plasma from the blood.

22. The method of claim 21, wherein the anticoagulant is selected from sodium citrate, ethylenelendiaminetetraacetic acid disodium salt, ethylenelendiaminetetraacetic acid dipotassium salt and combinations thereof.

* * * * *